United States Patent [19]

Matsuoka et al.

[11] Patent Number: 4,962,211

[45] Date of Patent: Oct. 9, 1990

[54] BIPHENYL DERIVATIVE AND PRODUCTION AND USE THEREOF

[75] Inventors: Yoshiyuki Matsuoka; Kunio Hosaka; Shigefumi Takeda; Hiroshi Mitsuhashi, all of Tokyo, Japan

[73] Assignee: Tsumura & Co., Tokyo, Japan

[21] Appl. No.: 445,977

[22] Filed: Nov. 21, 1989

Related U.S. Application Data

[63] Division of Ser. No. 180,107, filed as PCT JP87/00387 on Jun. 13, 1987, published as WO87/07605 on Dec. 17, 1987, Pat No. 4,904,694.

[30] Foreign Application Priority Data

Jun. 13, 1986 [JP] Japan .............................. 61-136262
Aug. 5, 1986 [JP] Japan .............................. 61-182628
Jun. 13, 1987 [WO] PCT Int'l Appl. ... PCT/JP87/00387

[51] Int. Cl.$^5$ ........................................... C07D 317/06
[52] U.S. Cl. ............................................... 549/436
[58] Field of Search ......................................... 549/436

[56] References Cited

U.S. PATENT DOCUMENTS 4,849,448  7/1989  Kimura et al. ..................... 549/436

OTHER PUBLICATIONS

Rapp et al., Chem. Ber., 105(1), 217–33 (1972).

*Primary Examiner*—Nicky Chan
*Attorney, Agent, or Firm*—Burns, Doane, Swecker & Mathis

[57] ABSTRACT

The present invention relates to a novel biphenyl derivative having a liver ailment-moderating action, which is effective for the remedy of liver diseases such as acute hepatitis and chronic hepatitis, a process for the preparation of this derivative and a liver ailment-moderating agent comprising this derivative as an active ingredient. Moreover, the present invention relates to a compound valuable as the intermediate compound for the synthesis of this derivative and a process for efficiently preparing this intermediate compound.

2 Claims, No Drawings

BIPHENYL DERIVATIVE AND PRODUCTION AND USE THEREOF

This application is a divisional, of application Ser. No. 07,180,107, filed as PCT JP87/00387 on Jun. 13, 1987, published as WO87/07605 on Dec. 17, 1987, now U.S. Pat. No. 4,904,694.

TECHNICAL FIELD

The present invention is related to a novel biphenyl derivative having a liver ailment-moderating action and effective for the remedy of acute hepatitis and chronic hepatitis, a process for the preparation thereof, and a liver ailment-moderating agent comprising the novel derivative as an effective ingredient.

BACKGROUND ART

It is said that there are 2,000,000 patients suffering from liver diseases such as acute hepatitis and chronic hepatitis in Japan at present, and it is known that dibenzocyclo-octadiene type lignins contained in fruits of *Schisandra chinesis BAILL* belonging to the genus Schisadraceae are valuable for the remedy of these liver diseases (Japanese Patent Application No. 60-122560). However, the development of a medicine having a greater liver ailment-moderating action is desired.

DISCLOSURE OF THE INVENTION

Research was made with a view to discovering a substance having a more effective liver ailment moderating action, and we have already proposed several compounds (Japanese Patent Application No. 60-136261). We continued this research, and found a novel compound represented by the formula (I) given below.

More specifically, in accordance with the present invention, there is provided a novel biphenyl derivative represented by the following formula (I):

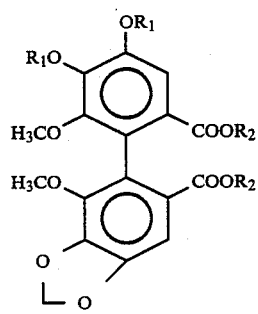

wherein $R_1$ and $R_2$ stand for a hydrogen atom or a methyl group.

BEST MODE FOR CARRYING OUT THE INVENTION

The compound of the formula (I) is prepared, for example, by subjecting a compound represented by the following formula (II):

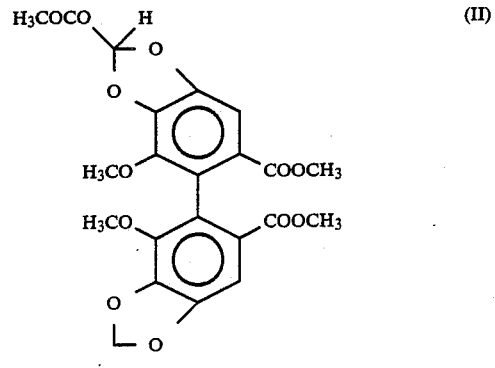

to at least one operation selected from hydrolysis and methylation.

The compound of the formula (II) as the starting compound can be obtained, for example, through the following steps (1) through (5).

(1) A commercially available alkyl ester of gallic acid is reacted with anhydrous potassium carbonate by using a methylating agent selected from iodomethane, dichloromethane and bromochloromethane in an organic solvent such as acetone or DMSO (dimethylsulfoxide) at 20° to 60° C. for 20 to 40 hours under an anhydrous condition, for example, in a nitrogen current to obtain a compound represented by the following formula (III):

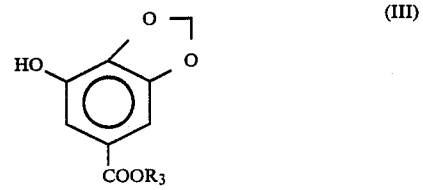

wherein $R_3$ stands for a hydrogen atom, a methyl group, an ethyl group or a propyl group.

(2) The compound of the formula (III) is halogenated to obtain a compound represented by the following formula (IV):

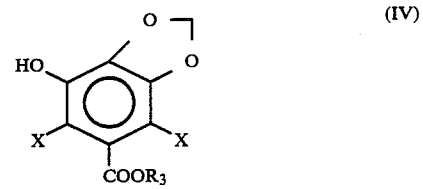

wherein $R_3$ as defined above and X stands for a halogen atom.

The halogenation is easily achieved by customary procedures. As specific examples of the halogen, there can be mentioned chlorine, bromine and iodine. As the reaction solvent, there can be mentioned acetic acid and chloroform, and a dissolution assistant such as DMF (dimethylformamide) may be used according to need. The reaction is completed within about 10 to 20 hours at a reaction temperature in the range of from −10° C. to room temperature. After termination of the reaction, the reaction mixture is poured into ice water and extracted with ether, 10% potassium carbonate or the like to obtain a compound of the formula (IV).

(3) The compound of the formula (IV) is reacted with zinc in the presence of a base to obtain a compound represented by the following formula (V):

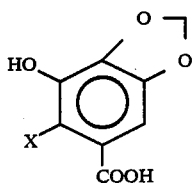

wherein X is as defined above.

As specific examples of the base, there can be mentioned sodium hydroxide and potassium hydroxide. The reaction temperature is 0° to about 30° C. and the reaction time is about 1 to 8 hours. By this reaction, the alkyl ester is hydrolyzed to form a carboxylic acid. Since the reaction product is precipitated in the reaction liquid, purification can be accomplished by such simple means as filtration and recrystallization.

Since the above reaction is a halogen substitution reaction at the 2- and 6-positions, the reaction is similarly advanced irrespective of the kinds of X and $R_3$.

(4) Then, the compound of the formula (V) is methylated and coupling is effected by utilizing the Ullmann reaction to obtain a compound represented by the following formula (VI):

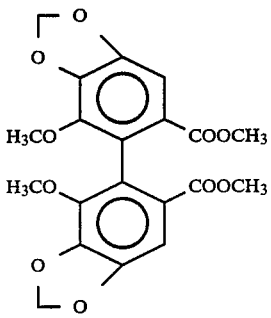

The methylation can be performed by using a methylating agent such as dimethyl sulfate according to customary procedures. In the Ullmann reaction, copper powder is incorporated into the methylation product, and preferably, the mixture is heated at 70° to 100° C. for about 3 to 6 hours under a reduced pressure and then heated at 130° to 160° C. for about 10 to 20 hours under atmospheric pressure. After termination of the reaction, the reaction mixture is extracted with an organic solvent to obtain a compound of the formula (VI).

(5) The compound of the formula (VI) is reacted with lead tetra-acetate in a solvent such as anhydrous benzene, preferably in an inert gas atmosphere, to obtain a compound represented by the formula (II).

The intermediate compound of the formula (V) obtained according to the above-mentioned process of the present invention is novel, and therefore, the present invention includes this compound of the formula (V).

The process for the preparation of the compound of the formula (V) according to the present invention is very valuable.

As the known process for synthesizing biphenyls having a skeleton similar to that of lignins, there can be mentioned a process of XIE et al (ACTA PHARMACEUTICA SINICA, Vol 17, No. 1, pages 23-27). According to this process of XIE et al, one of the hydroxyl groups at the meta-position of commercially available methyl gallate is selectively methylated to obtain a compound of the following formula A:

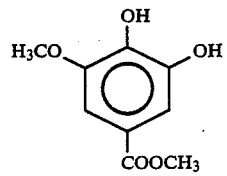

and this compound is reacted with diiodomethane in the presence of a base to obtain a compound represented by the following formula B:

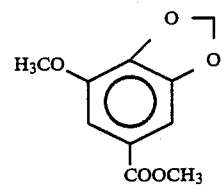

Then, the 6-position is brominated to obtain a compound of the following formula C:

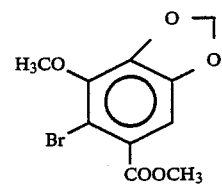

and coupling is effected by utilizing the Ullmann reaction to obtain a compound of the above-mentioned formula (VI).

In this process, three kinds of bromine compounds (2-bromo, 6-bromo and 2,6-dibromo compounds) are formed, and the yield of the 6-bromo compound is 10% and very low. Namely, a synthesis process in which bromine is selectively introduced in the 6-position in a high yield has not been developed.

Research was made with a view to developing a process for synthesizing a gallic acid derivative having a halogen atom such as bromine selectively introduced in the 6-position, and as a result, it was found that, if a halogen is introduced into the 2- and 6-positions and the halogen introduced in the 2-position selectively dissociated, the halogen can be selectively introduced in the 6-position.

Examples of the preparation of the compound of the formula (II) through the steps (1) to (5) will now be described.

Production Example 1

A mixture comprising 34 4 g of commercially available methyl gallate, 25.8 g of anhydrous potassium carbonate, 400 ml of DMSO and 50.0 g of diiodomethane was stirred at 40° C. for 24 hours in a nitrogen current. After the reaction, the liquid mixture was poured into water and made acidic by 2N hydrochloric acid, the mixture was extracted with ethyl acetate, and the extract was washed with water. The solvent was removed from the extract and the residue was subjected to flash column chromatography [466 g of 230–400 mesh silica gel, solvent n-hexane/acetone (3/1), pressure: 0.4 kg/cm$^2$, 5th to 9th fractions when fractions of 100 ml were collected] to effect purification and obtain 14.8 g of methyl 3-hydroxy-4,5-(methylenedioxy)benzoate (the yield was 40.4%).

Melting point 175° to 176° C.

Infrared absorption spectrum $$\nu_{max}^{KBr}$$

cm$^{-1}$:
3320, 2960, 2904, 1686, 1640, 1518, 1450, 1386, 1356, 1328, 1268, 1244, 1226, 1192, 1170, 1064.

Proton nuclear magnetic resonance spectrum [δ ppm in (CD$_3$)$_2$CO]:
8.71 (s, 1H), 7.25 (d, 1H, J=1.5 Hz), 7.01 (d, 1H, J=1.5 Hz), 6.06 (s, 2H), 3.81 (s, 3H).

Mass spectrum:
m/z (%) 196 (60, M+), 165 (100), 137 (23).

Production Example 2

In a mixed solvent of 75 ml of dimethylformamide and 100 ml of acetic acid was dissolved 11.19 g of methyl 3-hydroxy-4,5-(methylenedioxy)benzoate obtained in Production Example 1, and the solution was cooled at about −5° C. and a bromine solution (formed by diluting 6 ml of bromine with 50 ml of acetic acid) was dropped into the solution over a period of 1 hour. After the dropwise addition, the mixture was stirred for 15 hours and poured into ice water, the mixture was extracted with ether, and the extract was washed with water. The ether layer was then extracted with a 10% solution of potassium carbonate. The aqueous layer was made acidic by hydrochloric acid and extracted with ether, and the extract was washed with water and dried. The solvent was removed to obtain 16.8 g of methyl 2,6-dibromo-3-hydroxy-4,5-(methylenediox)benzoate (the yield was 83%).

Melting point: 132° to 133° C.

Infrared absorption spectrum $$\nu_{max}^{KBr}$$

cm$^{-1}$:
3300, 2912, 1720, 1606, 1502, 1462, 1440, 1404, 1374, 1316, 1284, 1218, 1176, 1094.

Proton nuclear magnetic resonance spectrum [δ ppm in (CD$_3$)$_2$CO]:
9.25 (bs, 1H), 6.17 (s, 2H), 3.90 (s, 3H).

Mass spectrum:
m/z (%) 356 (36, M+), 354 (74, M+), 352 (37, M+), 325 (49), 323 (100), 321 (51).

Production Example 3

In 40 ml of a 10% solution of sodium hydroxide was dissolved 3.54 g of methyl 2,6-dibromo-3-hydroxy-4,5-(methylenedioxy)benzoate obtained in Production Example 2, and 718 mg of powdery zinc was added to the solution and the mixture was stirred at room temperature for 1.5 hours. After the stirring, the mixture was filtered and the filtrate was made acidic (pH 1) by hydrochloric acid and the precipitated crystals were recovered by filtration, washed with water and dried to obtain 2.20 g of 6-bromo-5-hydroxy-3,4-(methylenedioxy)benzoic acid (the yield was 84.3%).

Melting point: 196° to 205° C.

Infrared absorption spectrum $$\nu_{max}^{KBr}$$

cm$^{-1}$:
3084, 1694, 1630, 1504, 1488, 1422, 1398, 1356, 1300, 1250, 1208, 1186, 1078.

Proton nuclear magnetic resonance spectrum [δ ppm in (CD$_3$)$_2$CO-D$_2$O]:
6.92 (s, 1H), 6.08 (s, 2H).

Mass spectrum:
m/z (%) 262 (45, M+), 260 (45, M+), 181 (18).

Production Example 4

A mixture comprising 2.20 g of 6-bromo-5-hydroxy-3,4-(methylenedioxy)benzoic acid obtained in Production Example 3, 2.9 g of anhydrous potassium carbonate, 2 ml of dimethyl sulfate and 30 ml of anhydrous acetone was stirred at room temperature in a nitrogen current for 16 hours. The reaction mixture liquid was poured into water and extracted with ether, and the extract was washed with water, shaken with a saturated aqueous solution of sodium chloride, and dried with anhydrous sodium sulfate. The solvent was removed to obtain 2.06 g of methyl 6-bromo-5-methoxy-3,4-(methylenedioxy)benzoate (the yield was 84.6%).

Melting point: 85.5° to 86° C.

Infrared absorption spectrum $$\nu_{max}^{KBr}$$

cm$^{-1}$:
2952, 2908, 1728, 1596, 1504, 1478, 1458, 1432, 1406, 1388, 1372, 1282, 1232, 1204, 1190, 1172, 1124, 1094, 1046.

Proton nuclear magnetic resonance [δ ppm in CDCl$_3$]:
7.03 (s, 1H), 6.03 (s, 2H), 4.01 (s, 3H), 3.88 (s, 3H).

Mass spectrum:
m/z (%) 290 (80, M+), 288 (85, M+), 259 (93), 257 (100).

Then, 50.5 g of the crystals of methyl 6-bromo-5-methoxy-3,4-(methylenedioxy)benzoate were sufficiently pulverized and mixed homogeneously with 240 g of active copper. The mixture was dried at 80° to 90° C. under a reduced pressure for 3 hours, and then the mixture was heated at 146° to 150° C. under atmospheric pressure for 15 hours. The reaction mixture was cooled and extracted with chloroform. The solvent was removed from the extract and the residue was washed with ether to obtain 31.0 g of crude crystals Recrystallization from a chloroform/methanol mixed solvent gave 29.64 g of dimethyl 2,2'-dimethoxy-3,3',4,4'-bis(methylenedioxy)1,1'-biphenyl-6,6'dicarboxylate (the yield was 82%).

Melting point: 208° to 208.5° C.

Infrared absorption spectrum $$\nu_{max}^{KBr}$$

cm$^{-1}$:
2992, 2952, 1720, 1616, 1500, 1476, 1434, 1410, 1396, 1364, 1282, 1222, 1166, 1116, 1086, 1042, 968, 938.

Proton nuclear magnetic resonance spectrum [δ ppm in CDCl$_3$]:

7 23 (s, 2H), 6.04 (s, 4H), 3.77 (s, 6H),
3.61 (s, 6H).
Mass spectrum:
m/z (%) 418 (100, M+), 328 (31), 223 (57).

Production Example 5

A mixture comprising 2.1 g of dimethyl 2,2'-dimethoxy-3,3',4,4'-bis(methylenedioxy)-1,1'-biphenyl-6,6-dicarboxylate obtained in Production Example 4, 3.3 g of lead tetra-acetate and 25 ml of anhydrous benzene was stirred for 22 hours in a nitrogen current After the reaction, the reaction mixture was extracted with ethyl acetate, and the solvent was removed from the extract and the residue was subjected to silica gel column chromatography [230–400 mesh silica supplied by Merk, solvent: n-hexane/acetone (3/1), pressure: 0.4 kg/cm$^2$, 55th to 65th fractions when fractions of 100 ml were collected] to effect purification and obtain 1 g of dimethyl 3,4-acetoxymethylenedioxy-2,2'-dimethoxy-3',4'-methylene-dioxy-1,1'-biphenyl-6,6'-dicarboxylate (the yield was 45.8%).

The following effects can be attained by practicing the present invention.

(1) The compound of the formula (V) according to the present invention is a novel compound not disclosed in any literature reference and is an important intermediate to be used for the synthesis of biphenyls having a liver ailment-moderating action.

(2) In the production of the compound of the formula (V), a halogen can be selectively introduced in the 6-position in a high yield.

(3) Since the product of the formula (V) is precipitated in the reaction liquid, isolation and purification can be accomplished by a simple means.

The compound of the formula (I) can be obtained by subjecting the compound of the formula (II) to at least one operation selected from hydrolysis and methylation in an optional order.

The hydrolysis can be accomplished by ordinary procedures using an acid such as hydrochloric acid, sulfuric acid or acetic acid, and the methylation can be accomplished by ordinary procedures using dimethyl sulfate, diazomethane or the like.

After the reaction, the product can be easily purified by such customary means as filtration and recrystallization.

Specific examples of the production of the compound of the formula (I) will now be described.

EXAMPLE 1

A mixture comprising 7 g of dimethyl 3,4-acetoxymethylenedioxy-2,2'-dimethoxy-3',4'-methylenedioxy-1,1'-biphenyl-6,6'-dicarboxylate obtained in Production Example 5 and 40 ml of 80% acetic acid was heated and refluxed for 4 hours in a nitrogen atmosphere. After termination of the reaction, the reaction mixture was allowed to stand and the precipitated crystal was recovered by filtration to obtain 5.2 g of dimethyl 3,4-dihydroxy-2,2'-dimethoxy-3',4'-methylenedioxy-1,1'-biphenyl-6,6'-dicarboxylate (the yield was 86 8%).

Melting point: 214° to 215° C.

Infrared absorption spectrum $$\nu_{max}^{KBr}$$

cm$^{-1}$:

3380, 2948, 1708, 1694, 1614, 1594, 1502, 1480, 1462, 1440, 1414, 1402, 1360, 1340, 1314, 1284, 1228, 1208, 1128, 1090, 1074, 1044.

Proton nuclear magnetic resonance spectrum ]δ ppm in (CD$_3$)$_2$CO]:

8.19 (s, 2H), 7.34 (s, 1H), 7.15 (s, 1H),
6.13 (s, 2H), 3.73 (s, 3H), 3.55 (s, 3H),
3.51 (s, 3H), 3.44 (s, 3H).

Mass spectrum:
m/z (%) 406 (M+, 49), 374 (100), 315 (83).

EXAMPLE 2

A mixture comprising 3.6 g of dimethyl 3,4-dihydroxy-2,2'-dimethoxy-3',4'-methylene-dioxy-1,1'-biphenyl-6,6'-dicarboxylate, 3.5 g of anhydrous potassium carbonate, 20 ml of acetone and 2.0 ml of dimethyl sulfate was stirred at room temperature for 15 hours After the reaction, the reaction mixture was poured into water and extracted with ethyl acetate, the solvent was removed from the extract, and the residue was recrystallized from methanol to obtain 3 6 g of dimethyl 2,2'3,4-tetramethoxy-3'4'-methylenedioxy-1,1'-biphenyl-6,6'-dicarboxylate (the yield was 96%).

Melting point 109° to 110° C.

Infrared absorption spectrum $$\nu_{max}^{KBr}$$

cm$^{-1}$:

2984, 2944, 1726, 1614, 1594, 1502, 1476, 1446, 1434, 1418, 1392, 1364, 1336, 1282, 1250, 1228, 1214, 1196, 1164, 1140, 1104, 1084, 1054, 1034, 1000.

Proton nuclear magnetic resonance spectrum [δ ppm in CDCl$_3$]:

7.37 (s, 1H), 7.25 (s, 1H), 6.06 (s, 2H),
3.94 (s, 6H), 3.78 (s, 3H), 3.65 (s, 3H),
3.61 (s, 3H), 3.59 (s, 3H).

Mass spectrum:
m/z (%) 434 (M+, 100), 223 (60).

EXAMPLE 3

In 20 ml of methanol was dissolved 1.75 g of dimethyl 2,2'3,4-tetramethoxy-3'4'-methylenedioxy-1,1'-biphenyl-6,6'-dicarboxylate obtained in Example 2, and 10 ml of a 10% aqueous solution of sodium hydroxide was added to the solution and the mixture was heated and refluxed for 16 hours. After termination of the reaction, the reaction mixture was cooled and the precipitated crystals were recovered by filtration and recrystallized from methanol to obtain 1.3 g of 2,2',3,4-tetramethoxy-3',4'-methylenedioxy-1,1'-biphenyl-6,6'-dicarboxylic acid (the yield was 81%).

Melting point: 243° to 243.5° C.

Infrared absorption spectrum $$\nu_{max}^{KBr}$$

cm$^{-1}$:

3700–2300 (br), 1692, 1614, 1594, 1566, 1500, 1478, 1464, 1414, 1388, 1364, 1334, 1280, 1228, 1200, 1180, 1140, 1110, 1086, 1036.

Proton nuclear magnetic resonance spectrum δ ppm in (CD$_3$)$_2$CO:

7.29 (s, 1H), 7.12 (s, 1H), 6.14 (1H), 6.12 (1H), 3.86 (s, 3H), 3.80(s, 3H), 3.66 (s, 3H), 3.47 (s, 3H).

Mass spectrum:

m/z (%) 406 (M+, 100), 209 (44).

The so-obtained compound of the formula (I) according to the present invention has a liver ailment-moderating action and is effective for the remedy of liver diseases. That the compound of the formula (I) has a liver ailment-moderating action will be illustrated with reference to the following experiment.

Experiment

Male SD strain rats of 7 weeks old were used as 10 animals in each group after the fasting for 24 hours. Each of the compounds obtained in Examples 1 through 3 was suspended in 1% Tween 80/physiological saline solution and administered at 100 mg/kg intraperitoneally. After 30 minutes, 4 mg/kg of a 25% carbon tetrachloride/olive oil mixture was orally administered to the rats. After 24 hours, blood was collected and the liver was extracted. In the control group, the above procedures were repeated in the same manner except that the compounds obtained in Examples 1 through 3 were not added.

The sGPT value (serum Glutamic Pyruvic Transaminase) of the control group was 6690±679, but the sGPT values of the groups to which the compounds obtained in Examples 1, 2 and 3 were administered were 1136±242, 713±109 and 1648±300, respectively.

From the foregoing results, it was confirmed that the compound of the formula (I) has a liver ailment-moderating action.

When the compounds obtained in Examples 1 through 3 were orally administered to mice of the ddY system (one group of 10 mice for each dose), it was found that no had mouse died at doses of up to 1000 mg/kg.

In view of the foregoing results, it is considered that an appropriate daily dose of the liver ailment-moderating agent of the present invention for adults is 10 to 100 mg as the weight of the compound of the formula (I) in the case of oral administration and 0.1 to 30 mg as the weight of the compound of the formula (I) in the case of non-oral administration, and the agent is preferably divided and administered several times a day.

As the result of our investigation, it was confirmed that the compound obtained in Production Example 4 also has a liver ailment-moderating action. This will now be illustrated with reference to the following referential examples.

Referential Example 1

Male SD strain rats of 7 weeks old were used as 10 animals in each group after the fasting for 24 hours. The compound obtained in Production Example 4 was suspended in 1% Tween 80/physiological saline solution and administered at 100 mg/kg intraperitoneally. After 30 minutes, 4 mg/kg of a 25% carbon tetrachloride/olive oil mixture was orally administered to the rats. After 24 hours, blood was collected and the liver was extracted. In the control group, the above procedures were repeated in the same manner except that the compound obtained in Production Example 4 was not added.

The sGPT value (serum Glutamic Pyruvic Transaminase) of the control group was 2040.56±310.17 but the sGPT value of the group to which 100 mg/kg of the compound obtained in Production Example 4 was administered was 314.4±45.79.

Referential Example 2

Male SD strain rats of 7 weeks old were used as 10 animals in each group after the fasting for 24 hours. The compound obtained in Production Example 4 was suspended in 1% Tween 80/refined water solution and administered at 100 mg/kg intraperitoneally. After 30 minutes, 2 ml/kg of a 25% carbon tetrachloride/olive oil mixture was orally administered to the rats. After 24 hours, blood was collected from the celiac artery and the sGOT value (serum Glutamic Oxaloacetic Transaminase) and the sGPT value were measured. The results are shown in Table 1.

TABLE 1

| Medicine | sGOT Values (units/l) | sGPT Values (units/l) |
|---|---|---|
| untreated group | 67.2 ± 3.3 | 11.4 ± 0.8 |
| control | 7704.4 ± 1281.3 | 981.4 ± 158.5 |
| compound obtained in Production Example 4 | 4278.8 ± 1483.6 | 572.0 ± 190.7 |

From the foregoing results, it was confirmed that the compound of the formula (I) according to the present invention has a liver ailment-moderating action.

The compound of the formula (I) according to the present invention can be formed into pharmaceutical preparations such as liquid preparations, powdered medicines, granules, tablets, enteric coatings and capsules by using appropriate solvents, excipients and adjuvants customarily used for medicines according to customary pharmaceutical procedures.

Other medicinally active components may be mixed with the compound of the present invention when forming these pharmaceutical preparations.

For the oral administration, the compound of the present invention is formed into tablets, pills, capsules, powders and granules by using at least one excipient selected from starch, lactose, refined sugar, mannitol, carboxymethyl cellulose and the like.

For these preparations, in addition to the excipient, there can be used lustering agents such as magnesium stearate, sodium lauryl sulfate and talc, binders such as dextrin, crystalline cellulose, polyvinyl pyrrolidone, gum arabic, corn starch and gelatin, disintegrating agents such as sodium cellulose glucolate, potassium cellulose glucolate, potato starch and carboxymethyl cellulose, and flowability improvers such as soft anhydrous silicic acid. The medicinal compound of the present invention can be administered in the form of a suspension, an emulsion, a syrup or an elixir. A taste improver, a smell improver, and a colorant may be incorporated into these preparations.

When preparing an injection, distilled water for injection, physiological saline solution, an aqueous solution of dextrose, a vegetable oil for injection, propylene glycol or polyethylene glycol can be used as the diluent. Furthermore, an isotactic agent, a stabilizer, an antiseptic agent, an analgetic agent or the like may be added according to need. Preferably, the preparation of this type is dissolved in a sterilized solution for injection.

INDUSTRIAL APPLICABILITY

A compound which has a liver ailment-moderating agent and is effective for the remedy of liver diseases and a liver ailment-moderating agent containing this compound are provided according to the present invention. Furthermore, a process for advantageously preparing this compound and an intermediate compound for the preparation of this compound are provided according to the present invention.
We claim:
1. A compound having the following formula (V):
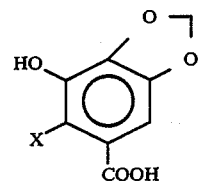
wherein X represents a halogen atom.
2. The compound as defined in claim 1, wherein said halogen is chlorine, bromine or iodine.
* * * * *